(12) United States Patent
Mest et al.

(10) Patent No.: US 8,333,762 B2
(45) Date of Patent: Dec. 18, 2012

(54) IRRIGATED CATHETER WITH IMPROVED IRRIGATION FLOW

(75) Inventors: Robert A. Mest, Long Beach, CA (US); Jeffrey William Schultz, La Verne, CA (US)

(73) Assignee: Biosense Webster, Inc., Diamond Bar, CA (US)

(*) Notice: Subject to any disclaimer, the term of this patent is extended or adjusted under 35 U.S.C. 154(b) by 1081 days.

(21) Appl. No.: 11/966,899

(22) Filed: Dec. 28, 2007

(65) Prior Publication Data
US 2009/0306649 A1 Dec. 10, 2009

(51) Int. Cl.
*A61B 18/14* (2006.01)

(52) U.S. Cl. .......................................... 606/41
(58) Field of Classification Search ....................... 606/41
See application file for complete search history.

(56) References Cited

U.S. PATENT DOCUMENTS

| | | | |
|---|---|---|---|
| 4,407,302 A * | 10/1983 | Hirshorn et al. | 607/121 |
| 5,697,927 A * | 12/1997 | Imran et al. | 606/41 |
| 5,800,432 A | 9/1998 | Swanson | |
| 5,964,757 A | 10/1999 | Ponzi | |
| 6,002,956 A | 12/1999 | Schaer | |
| 6,047,700 A | 4/2000 | Eggers et al. | |
| 6,198,974 B1 * | 3/2001 | Webster, Jr. | 607/122 |
| 6,569,162 B2 * | 5/2003 | He | 606/41 |
| 6,602,242 B1 | 8/2003 | Fung et al. | |
| 6,611,699 B2 | 8/2003 | Messing | |
| 6,662,034 B2 | 12/2003 | Segner et al. | |
| 2005/0177151 A1 | 8/2005 | Coen et al. | |
| 2009/0163913 A1 * | 6/2009 | Wang et al. | 606/41 |

* cited by examiner

*Primary Examiner* — Lee S Cohen
(74) *Attorney, Agent, or Firm* — Christie, Parker & Hale, LLP

(57) ABSTRACT

An irrigated ablation catheter provides improved distribution of irrigation fluid across its tip electrode surface resulting in improved cooling and flushing of blood and proteins from the tip region. An axially directed flow of irrigation provides improved heat transfer from the tip electrode to the irrigation fluid allowing for a cooler tip electrode and larger lesions. The irrigation fluid is introduced to the catheter with improved flow by means of a standard constant flow pump. A lumen or tube within a shaft of the catheter transfers the irrigation fluid to a proximal end of the tip electrode where it exits the catheter via a flow directing member mounted on the tip electrode. In one embodiment, the flow directing member is a thin walled tube that surrounds the proximal end of the tip electrode and directs the irrigation fluid distally along an outer surface of the tip electrode.

16 Claims, 14 Drawing Sheets

IRRIGATED CATHETER WITH IMPROVED IRRIGATION FLOW

FIELD OF INVENTION

The present invention relates to ablation catheters, and in particular to irrigated ablation catheters.

BACKGROUND

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

In certain applications, it is desirable to have an irrigated tip catheter in order to cool the tip electrode at the site of ablation and to prevent thrombus.

A typical ablation procedure involves the insertion of a catheter having a tip electrode at its distal end into a heart chamber. A reference electrode is provided, generally taped to the skin of the patient. RF (radio frequency) current is applied to the tip electrode, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause a lesion. Heating of the electrode results from conduction from the heated tissue. While the blood circulating around the ablation electrode tends to cool it, a stagnant area between the electrode and the tissue may be heated to such a temperature that a thin coating of blood protein forms on the surface of the tip electrode. This can cause an impedance rise and/or a thrombus that could become an embolus. When this occurs, the catheter should be removed and the tip electrode cleaned.

When RF current is applied to an ablation electrode in good contact with the endocardium to create a lesion, the amount of power delivered is limited by the heating of the electrode in order to prevent char and thrombus. The resulting lesion tends to be hemispherical, usually about 6 mm in diameter and about 3 to 4 mm deep.

When a tip electrode is irrigated, e.g., with room temperature saline, the tip electrode is cooled by the flow of saline through it and the surface of the electrode is flushed. Because the strength of the RF current is no longer limited by the interface temperature, current can be increased. This results in lesions which tend to be larger and more spherical, usually measuring about 10 to 12 mm.

Current irrigated catheters utilize either closed or open fluid systems. Open irrigation fluid systems use holes placed in specific locations around the tip electrode to distribute the irrigation fluid. These designs do not provide uniform fluid distribution along the outer surface of the tip electrodes. Additionally, the irrigation fluid is projected far from the tip electrode and does not provide a uniform and complete boundary layer from the surrounding blood. Accordingly, it is desirable to provide an irrigated catheter with a generally complete and uniform boundary layer reducing direct blood contact with the tip electrode during the application of RF energy. With maintained irrigation fluid-to-tip electrode contact, such an improved catheter will provide increased heat loss including convective heat loss resulting in more efficient cooling and thrombus prevention.

SUMMARY OF THE INVENTION

The present invention is directed to an irrigated ablation catheter that provides improved distribution of irrigation fluid across its tip electrode surface resulting in improved cooling and flushing of blood and proteins from the tip region. An axially directed flow of irrigation provides improved heat transfer from the tip electrode to the irrigation fluid allowing for a cooler tip electrode and larger lesions.

The irrigation fluid is introduced to the catheter with improved flow by means of a standard constant flow pump. A lumen or tube within a shaft of the catheter transfers the irrigation fluid to a proximal end of the tip electrode where it exits the catheter via a flow directing member mounted on the tip electrode. In one embodiment, the flow directing member is a thin walled tube that surrounds the proximal end of the tip electrode and directs the irrigation fluid distally along an outer surface of the tip electrode.

The flow directing member is intended to evenly distribute the irrigation flow over the tip electrode, thus providing several benefits, including improved flushing of blood from the tip electrode surface and improved convective cooling of the tip electrode and tissue-to-tip electrode interface.

Improved flushing of blood from the tip electrode can more efficiently reduce or eliminate formation of coagulation on the tip electrode associated with the denaturing of proteins during RF application. By creating a generally uniform boundary layer of irrigation fluid around the tip electrode, blood is kept from the tip electrode or it is diluted such that the quantity of proteins exposed to high heat levels during RF ablation is significantly decreased. Additionally, the generally uniform flow of irrigation fluid along the tip electrode tends to ensure that blood or blood protein contact with heat is momentary.

The catheter increases heat loss including convective heat loss by the tip electrode to the irrigation fluid by containing the irrigation fluid along the outer surface of the proximal portion of the tip electrode. By using the outer surface of the trip electrode as the cooling interface rather than internal cooling channels, the convective heat loss can be greatly increased due to the larger surface area provided by the outer surface of the tip electrode. It is also contemplated that the outer surface 63 can be texturized or roughen (see FIG. 6A) to increase the surface area for further increased convective heat loss. Heat fins 65 (see FIG. 6B) can also be added to the tip electrode for further increased convective heat loss. The flow directing member is configured to also direct the fluid along the distal end of the tip selectrode providing for additional convective heat loss.

During RF application, the improved fluid flow along the tip electrode provides more efficient convective heat loss, which could lead to a lower fluid flow rate and thus a decrease in delivery of fluid to the ablation site over the course of the procedure. In one embodiment, the catheter has a catheter body and a tip section adapted for ablation and irrigation. The tip section has a tip electrode and a flow directing member positioned over the tip electrode to direct fluid to flow over an outer surface of the tip electrode. The flow directing member is tubular having an inner surface that is supported away from the outer surface of the tip electrode by ribs extending longitudinally along the inner surface of the flow directing member. Gaps formed by the ribs define fluid channels that guide the fluid to flow over the outer surface of the tip electrode.

In a more detailed embodiment, the tip section also has a fluid cavity immediately proximal the tip electrode wherein fluid fed by the catheter body enters the cavity to come in contact with the outer surface of the tip electrode. To protect components extending through the cavity and into the tip electrode, connective tube are provided to bridge the cavity and isolate the components from exposure to the fluid. One or more connective tubes are notched at their distal end to prevent the distal end from cutting into the components, particularly those extending at an angle to the connective tubes.

In one embodiment, the catheter includes a temperature sensing means positioned to sense temperature at or near a center of a tip electrode. The temperature sensing means can be positioned to sense temperature omnidirectionally with respect to tissue-contacting surface of the tip electrode. Where the temperature sensing means comprises thermocouple wires, distal ends thereare of are positioned at or near a center of a semi-spherically configured distal end of the tip electrode for omnidirectional temperature sensing.

The catheter may be nondeflectable, deflectable by one or more puller wires, or guided by magnetic steering or a deflectable guiding sheath. The catheter may also contain an electromagnetic location sensor. One or more ring electrodes may also be provided distally from the tip electrode.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
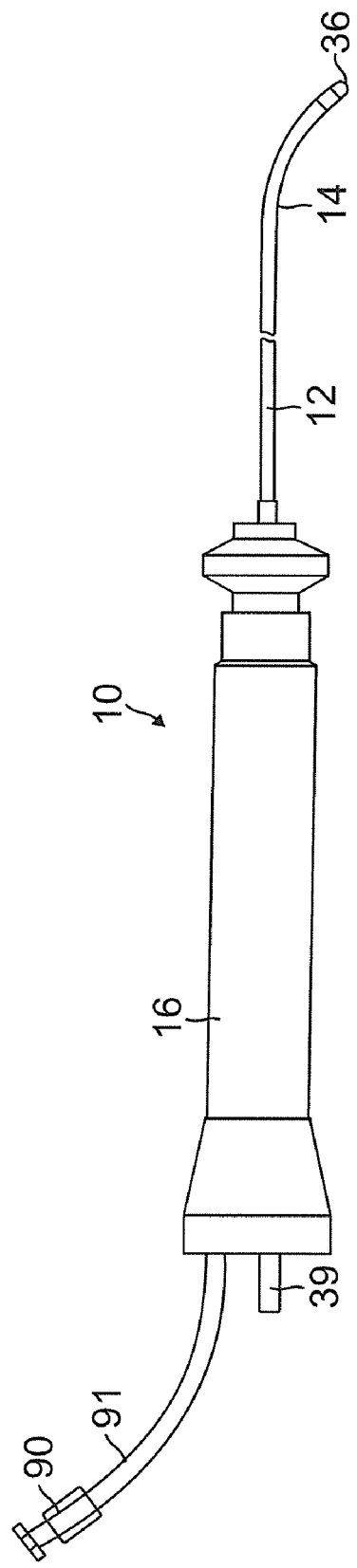
FIG. 1 is a side view of an embodiment of the catheter of the present invention.

As shown in FIGS. 1-8 catheter 10 of the present invention comprises an elongated catheter body 12 having proximal and distal ends, a deflectable (uni- or bi-directionally) intermediate section 14 at the distal end of the catheter body 12, a tip section 36 at the distal end of the intermediate section, and a control handle 16 at the proximal end of the catheter body 12.

Figure 2A:
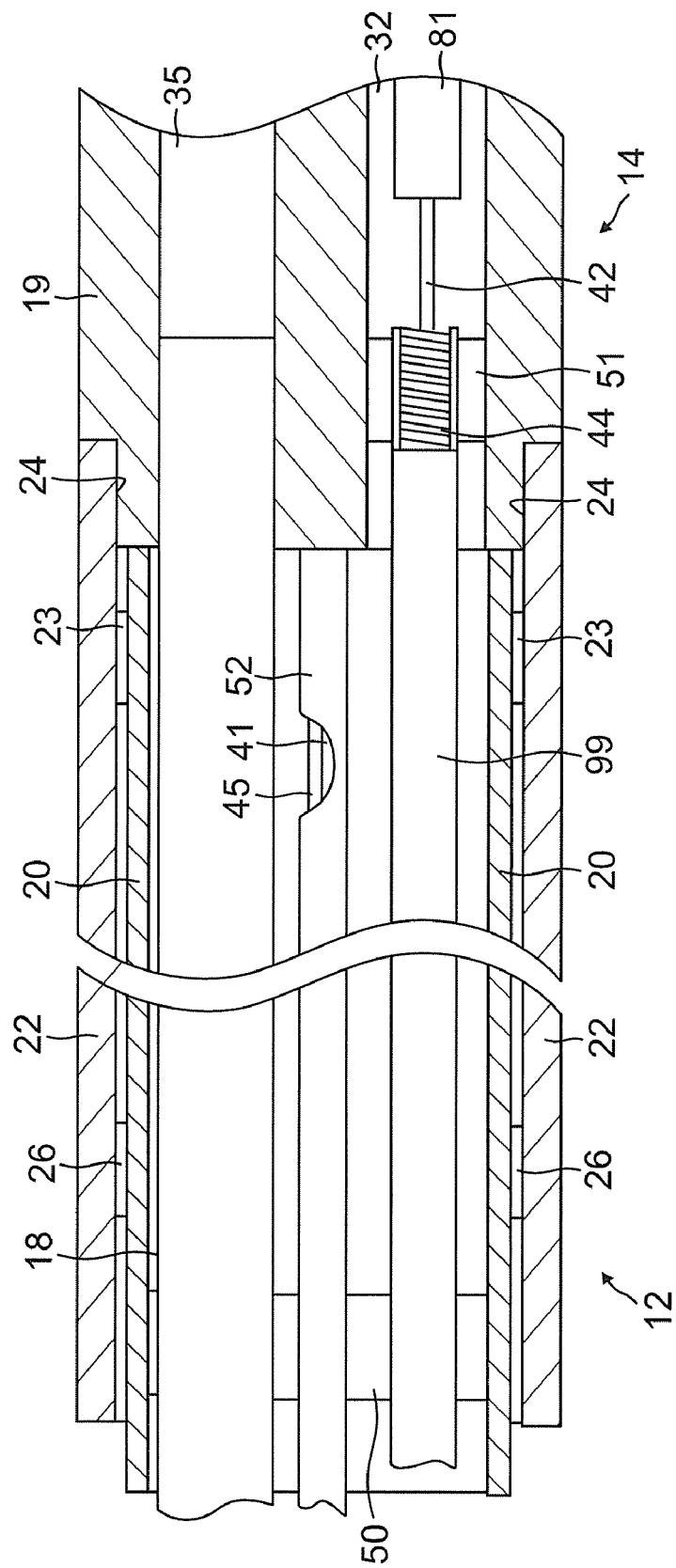
FIG. 2A is a side cross-sectional view of an embodiment of a catheter according to the invention, including a junction between a catheter body and an intermediate section, taken along a first diameter.
Figure 2B:
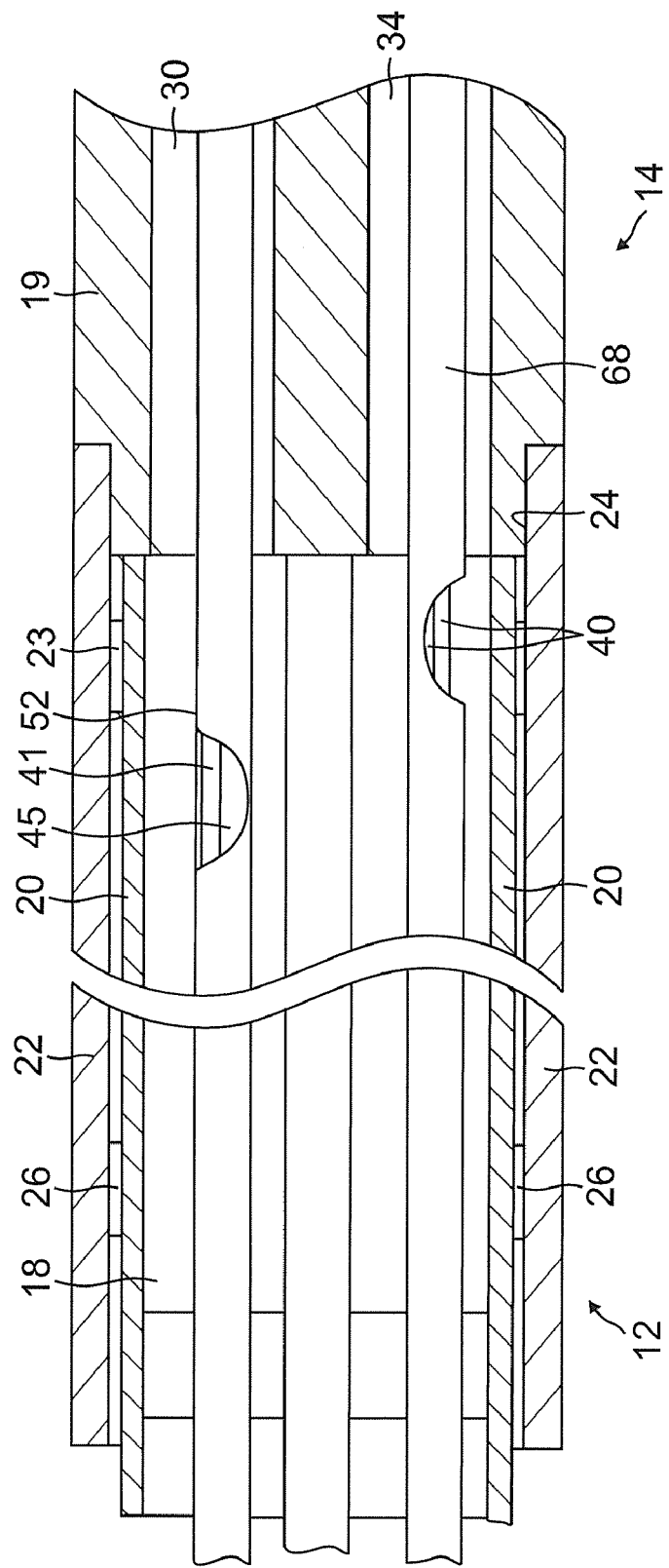
FIG. 2B is a side cross-sectional view of an embodiment of a catheter according to the invention, including the junction between the catheter body and the intermediate section, taken along a second diameter generally perpendicular to the first diameter of FIG. 2A.

With additional reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A construction comprises an outer wall 22 made of an extruded plastic. The outer wall 22 may comprise an imbedded braided mesh of stainless steel or the like to increase torsional stiffness of the catheter body 12 so that, when the control handle 16 is rotated, the catheter body 12, the intermediate section 14 and the tip section 36 of the catheter 10 will rotate in a corresponding manner.

Extending through the single lumen 18 of the catheter body 12 are components, for example, lead wire 40 and thermocouple wires 41, 45 protected by a sheath 52, a first irrigation tube segment 88, a compression coil 56 through which a puller wire 42 extends. A single lumen catheter body can be preferred over a multi-lumen body because it has been found that the single lumen body permits better tip control when rotating the catheter. The single lumen permits the various components such as the lead wire, thermocouple wires, infusion tube, and the puller wire surrounded by the compression coil to float freely within the catheter body. If such wires, tube and cables were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate the aforementioned components. The inner surface of the outer wall 22 may be lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing may be preferred for the stiffening tube 20 because it may be very thin walled while still providing very good stiffness. This maximizes the diameter of the central lumen 18 without sacrificing strength and stiffness.

The catheter may have an outer wall 22 with an outer diameter of from about 0.090 inch to about 0.104 inch and an inner diameter of from about 0.061 inch to about 0.075 inch and a polyimide stiffening tube 20 having an outer diameter of from about 0.060 inch to about 0.074 inch and a wall thickness of about 0.001-0.005 inch.

Figure 3A:
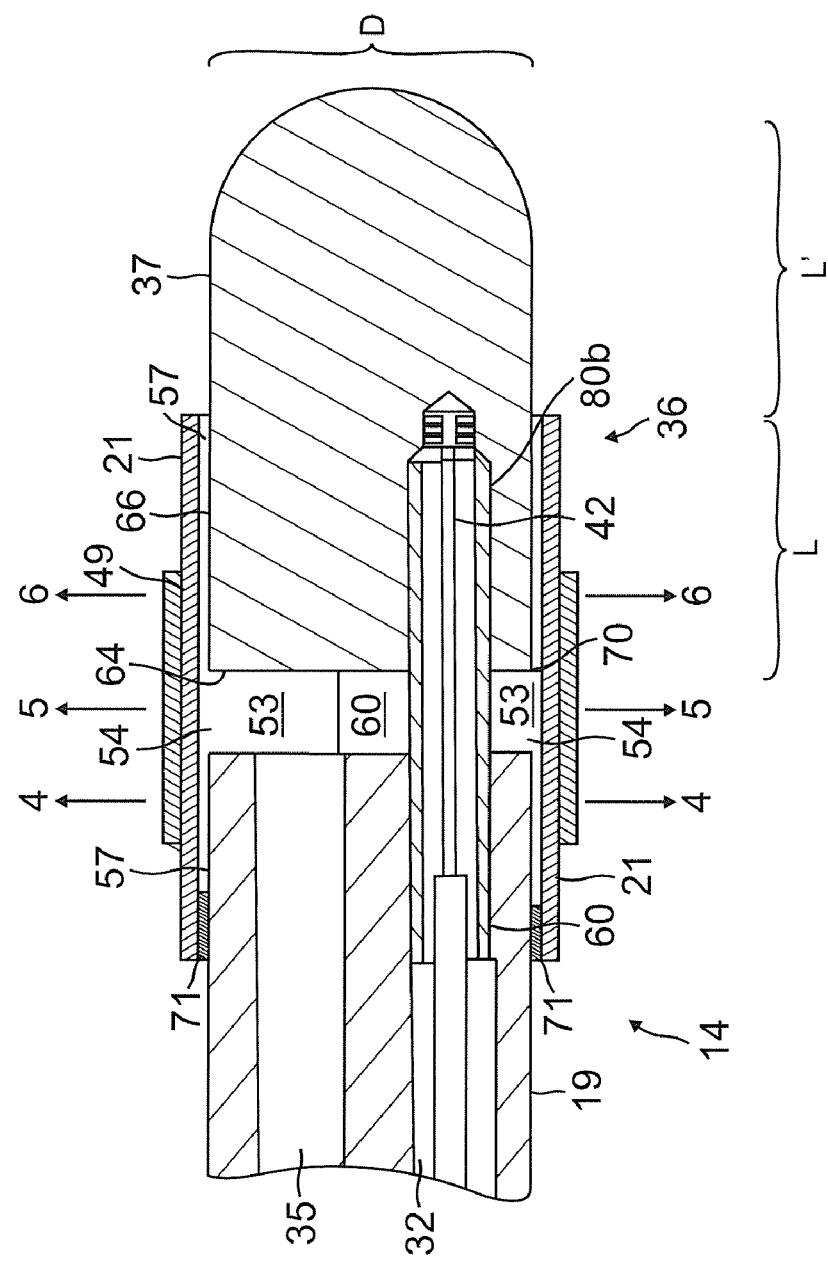
FIG. 3A is a side cross-sectional view of an embodiment of a catheter according to the invention, including a junction between the intermediate section and a tip section, taking along the first diameter.
Figure 3B:
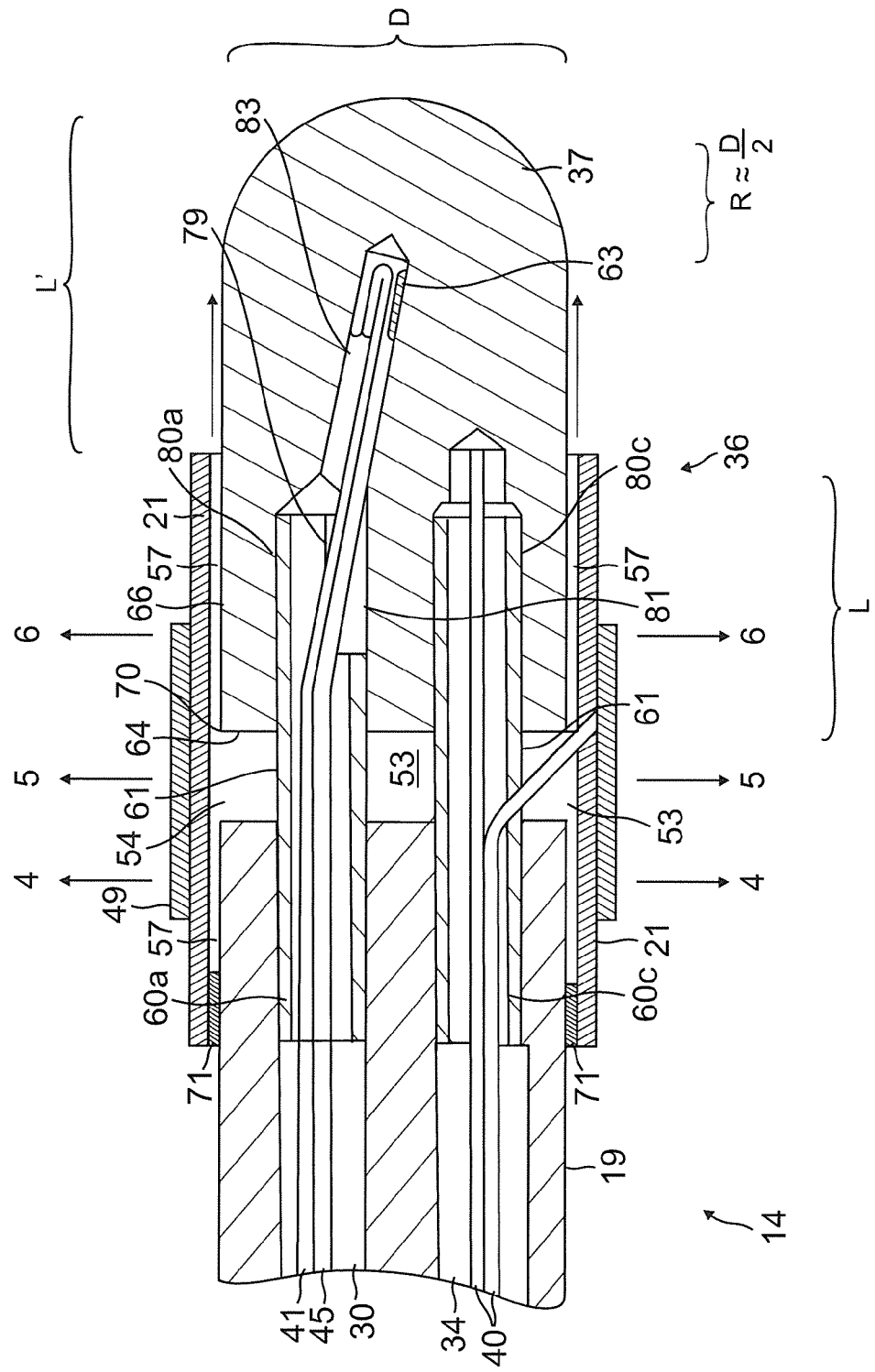
FIG. 3B is a side cross sectional view of an embodiment of a catheter according to the invention, including a junction between the intermediate section and a tip section, taken along a second diameter generally perpendicular to the first diameter of FIG. 3A
Figure 4:
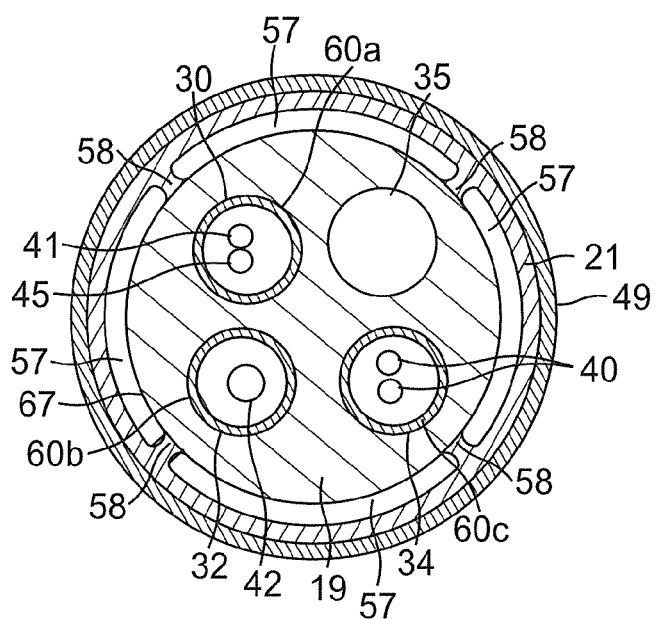
FIG. 4 is a longitudinal cross-sectional view of an embodiment of the tip section of FIGS. 3A and 3B, taken along line 4-4.

Referring also to FIGS. 3A, 3B and 4, the intermediate section 14 distal of the catheter body 12 comprises a shorter section of tubing 19 having multiple lumens. The tubing 19 is made of a suitable non-toxic material that is preferably more flexible than the catheter body 12. A suitable material for the tubing 19 is polyurethane braided with a low to medium durometer plastic. The outer diameter of the intermediate section 14, like that of the catheter body 12, is preferably no greater than about 8 french, more preferably 7 french. The size and number of the lumens is not critical. In an embodiment, the intermediate section 14 has an outer diameter of about 7 french (0.092 inch). The tubing has four off-axis lumens 30, 32, 34 and 35 that are generally about the same size, each having a diameter of from about 0.020 inch to about 0.024 inch, preferably 0.022 inch.

Referring to FIGS. 2A and 2B, the catheter body 12 may be attached to the intermediate section 14 comprises an outer circumferential notch 24 configured in the proximal end of the tubing 19 that receives the inner surface of the outer wall 22 of the catheter body 12. The intermediate section 14 and catheter body 12 are attached by glue or the like. Before the intermediate section 14 and catheter body 12 are attached, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the intermediate section 14. If no compression coil is used, a force is applied to the proximal end of the stiffening tube 20, and, while the stiffening tube 20 is under compression, a first glue joint (not shown) is made between the stiffening tube 20 and the outer wall 22 by a fast drying glue, e.g. cyanoacrylate. Thereafter a second glue joint 26 is formed between the proximal ends of the stiffening tube 20 and outer wall 22 using a slower drying but stronger glue, e.g., polyurethane.

If desired, a spacer can be located within the catheter body between the distal end of the stiffening tube and the proximal end of the tip section. The spacer provides a transition in flexibility at the junction of the catheter body and intermediate section, which allows this junction to bend smoothly without folding or kinking. A catheter having such a spacer is described in U.S. patent application Ser. No. 08/924,616, entitled "Steerable Direct Myocardial Revascularization Catheter", the entire disclosure of which is incorporated herein by reference.

With reference to FIGS. 1, 2B and 4, to energize tip and ring electrodes at or near the tip section 36 for RF ablation, lead wires 40 extend through the lumen 34 of intermediate section 14, the central lumen 18 of the catheter body 12, and the control handle 16, and terminates at its proximal end in an input jack (not shown) or connector 77 that may be plugged to an generator or the like (not shown). The portion of the lead wire 40 extending through the central lumen 18 of the catheter body 12, control handle 16 and distal end of the intermediate section 14 is enclosed within a protective sheath 68, which can be made of any suitable material, preferably Teflon®. The protective sheath is anchored at its distal end to the proximal end of the intermediate section 14 by gluing it in the lumen 34 with polyurethane glue or the like.

A temperature sensing means is provided for the tip section 36 as explained in detail further below. Any conventional temperature sensing means, e.g., a thermocouple or thermistor, may be used. With reference to FIGS. 2B and 4, a suitable temperature sensing means for the tip section comprises a thermocouple formed by a wire pair. One wire of the wire pair is a copper wire 41, e.g., a 40 gauge or similar size copper wire. The other wire of the wire pair is a constantan wire 45, which gives support and strength to the wire pair. The wires 41 and 45 extend through the lumen 34 in the intermediate section 14. Within the catheter body 12 the wires 41 and 45 extend through the central lumen 18 within the protective sheath 52. The wires 41 and 45 then extend out through the control handle 16 and to the connector 77. Alternatively, the temperature sensing means may be a thermistor. A suitable thermistor for use in the present invention is Model No. AB6N2-GC14KA143T/37C sold by Thermometrics (N.J.).

Referring to FIGS. 2A and 4, the puller wire 42 for deflecting the intermediate section 14 extends through the lumen 32 of the tubing 19 of the intermediate section and the catheter body 12 and is anchored at its proximal end to the control handle 16. The puller wire is made of any suitable metal, such as stainless steel or Nitinol, or fiber such as Spectra or Vectran, and is preferably coated with Teflon™ or the like. The coating imparts lubricity to the puller wire. The puller wire preferably has a diameter ranging from about 0.006 to about 0.012 inches. A compression coil 44 is situated within the catheter body 12 in surrounding relation to the puller wire. The compression coil 44 extends from the proximal end of the catheter body 12 to the proximal end of the intermediate section 14. The compression coil is made of any suitable metal, preferably stainless steel, and is tightly wound on itself to provide flexibility, i.e., bending, but to resist compression. The inner diameter of the compression coil is preferably slightly larger than the diameter of the puller wire 42. The Teflon® coating on the puller wire allows it to slide freely within the compression coil. If desired, particularly if the lead wire 40 is not enclosed by the protective sheath 52, the outer surface of the compression coils can be covered by a flexible, non-conductive sheath 99, e.g., made of polyimide tubing, to prevent contact between the compression coils and any other wires within the catheter body 12.

As shown in FIG. 2A, the compression coil 44 is anchored at its proximal end to the proximal end of the stiffening tube 20 in the catheter body 12 by glue joint 50 and at its distal end to the intermediate section 14 by glue joint 51. Both glue joints 50 and 51 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil. Within the lumen 32 of the intermediate section 14, the puller wire 42 extends through a plastic, preferably Teflon®, sheath 81, which prevents the puller wire 42 from cutting into the wall of the intermediate section 14 when the intermediate section is deflected. Longitudinal movement of the puller wire 42 relative to the catheter body 12, which results in deflection of the tip section 36, is accomplished by suitable manipulation of the control handle 16. Suitable control handles are described in U.S. Pat. No. 6,602,242, the entire disclosure of which is hereby incorporated by reference.

Extending from the distal end of the intermediate section 14 is the tip section 36 that includes a tip electrode 37 and a fluid directing member 21 as shown in FIGS. 3A and 3B. Extending between the distal end of the tubing 19 of the intermediate section 14 and the proximal end of the tip electrode 37 are connective tubes 60 that secure the tip electrode. Each connective tube also has an exposed mid-section 61 not covered by either the tubing 19 or the tip electrode 37 such that there is a gap 53 between the distal end of the tubing 19 and the proximal end of the tip electrode 37. Purposefully separated from each other, the distal end of the tubing 19 and the proximal end of the tip electrode 37 define a cavity 54 for receiving fluid in an otherwise confined tip section. Covering the gap and further defining the cavity is the fluid directing member 21 which is mounted over the distal end of the tubing 19 and the proximal end of the tip electrode.

In the illustrated embodiment, the fluid directing member 21 is generally cylindrical (or otherwise being of an atraumatic configuration) and tubular with an inner surface 56 configured with longitudinal ribs 58 that create a circumferential gap 57 between the inner surface 56 and an outer surface 63 of the tip electrode or an outer surface 69 of the tubing 19. As explained below in further detail, the fluid cavity 54 and the circumferential gap or channel 57 allow fluid fed through the catheter shaft 12 and intermediate section 14 to facilitate convective heat loss in the tip electrode which minimizes contacting tissue damage during ablation. The gap at the proximal end of the member 21 is occluded or otherwise sealed by a plug 71 so that the fluid is directed to exit at the distal end of the member 21. Suitable materials for sealing the gap include polyurethane or other material used for bonding the member to the tubing 19. A clasp or outer ring may be used. The bonding may even be accomplished thermally if appropriate materials are chosen. Accordingly, by providing the fluid cavity 54 and a generally continuous fluid flow over the tip electrode exiting the channel 57, lower tissue resistance can be maintained and larger lesions can be formed at lower powers and/or time settings. In the disclosed embodiment, the member 21 is constructed of a plastic material, e.g., polyetheretherketone (PEEK). However, as understood by one of ordinary skill in the art, the construction may be of any material that can be mounted over the gap 53 and provide sufficient structural strength to provide the channel 57. In the illustrated embodiment, there are four longitudinal ribs 58 equi-angular about the longitudinal axis of the tip electrode 37. The cross sectional shape and the plurality of ribs may be varied, so long as the ribs sufficiently support the inner surface 56 of the member 21 from fully contacting the tip electrode. In that regard, there plurality of the ribs may range from at least two or more, preferably from at least three or more, and more preferably from at least four or more.

To irrigate the tip section for convective heat loss, the lumen 35 at its distal end opens into the fluid chamber 54 which is generally filled with fluid, e.g., saline, transferred by the lumen 35. In accordance with a feature of the present invention, heat convention loss occurs between the tip electrode and the irrigation fluid fed through the lumen 35. The flow directing member 21 provides a means of forcing the fluid to flow across a face 64 and radial surface 66 of the proximal end of the tip electrode creating forced convention between the electrode and fluid. To that end, by increasing the diameter D of the tip electrode and/or the length L of the member 21 covering the tip electrode 37, a convective heat loss surface A including the face 64 and the radial surface 66 can be increased, which would in turn increase the convective heat loss of the tip electrode to the fluid, as defined by the following equation:

$$q = hA(dT/dt)$$

where,
  h=convective heat transfer coefficient
  $A = (1/4)\pi D^2 + \pi DL$
  dT/dt=difference in temperature of tip electrode and fluid with respect to time Advantageously, a proximal edge 70 (circumscribing the proximal face 66) of the tip electrode 37 is covered by the flow directing member 21. As such, the edge 70 (an area often of high energy density) is included in the convective heating loss surface A that is flushed with cooling fluid to minimize edge effect heating that would otherwise cause coagulation. Moreover, as also understood by one of ordinary skill in the art, an exposed length L' of the tip electrode is generally equal to the diameter D of the tip electrode so that the amount of contacting surface of the distal end with tissue can be generally constant regardless of the angle of contact (see FIG. 8). In that regard, a profile of the tip electrode in the exposed length L' has a generally straight proximal portion of a length equal to about (R/2) and a curved distal portion equal to about ($\pi r/2$), where R is the radius of the tip electrode (or D/2).

The tip electrode 37 can have an total length from the proximal face to the distal end ranging between about 2.0 mm and 8.0 mm, and preferably about 3.0 mm and 5.0 mm. In accordance with a feature of the present invention, the flow directing member 21 should cover at least a percentage of the total length of the tip electrode, where the percentage ranges between about 25 and 75, and preferably about 50. The member 21 therefore can have a total length ranging between about 3.0 mm and 7.0 mm, and preferably about 4.5 mm and 6.0 mm.

To isolate and protect the various components extending between the distal end of the tubing 19 and the tip electrode from fluid in the fluid chamber 54, the connective tubes 60 bridge the gap with their proximal ends received in selected lumens of the tubing 19 and their distal ends inserted into blind holes formed in the proximal end of the tip electrode. The connective tubes can be stainless steel hypo-tubes or any other suitable tube segments In the illustrated embodiment, there are three connective tubes 60a, 60b and 60c (see FIGS. 3A, 3B, 6 and 7. Tube 60a extends between the lumen 30 and a blind hole 80a, isolating thermocouple wires 41 and 45. Tube 60b extends between the lumen 32 and a blind hold 80b, isolating the puller wire 42. Tube 60c extends between the lumen 34 and a blind hole 80c, isolating the lead wires 40. As mentioned, lumen 35 opens into the gap so fluid can fill the gap and flow over the proximal face and proximal radial surface of the tip electrode as directed by the fluid directing member 21.

The blind holes 80 are formed in the tip electrode to allow components to be anchored tip electrode. The lead wire 40 is attached to the tip electrode 37 by any conventional technique. In the illustrated embodiment, connection of the lead wire 40 to the tip electrode 37 is accomplished, by welding the distal end of the lead wire into the blind hole 80c (FIG. 3B) in the tip electrode 37. It is noted that a ring electrode 49 is provided in the illustrated embodiment. The ring electrode is mounted over the flow directing member 21 with its lead wire 40 extending through holes provided in the connective tube 60c and in the flow directing member 21.

The tip electrode also has a blind hole 80c for anchoring the distal end of the puller wire. The blind hole 80c is generally longitudinally aligned with the lumen 32 of the tubing 19 of the intermediate section 14. (As understood by one of ordinary skill in the art, the distal end of the puller wire can also be anchored in the side wall of tubing 19 at the distal end of the intermediate section 14.) Likewise, the blind hole 80b for the lead wires is generally longitudinally aligned with the lumen 34. A method for anchoring the puller wire 42 within the tip electrode 37 is by crimping metal tubing 46 to the distal end of the puller wire 42 and soldering the metal tubing 46 inside the blind hole 101. Anchoring the puller wire 42 within the tip electrode 37 provides additional support, reducing the likelihood that the tip electrode 37 will fall off. Alternatively, the puller wire 42 can be attached to the side wall of the tubing 19 at the distal end of the intermediate section 14.

In accordance with a feature of the present invention, the blind hole 80a extends deeply into the tip electrode 37 so that the thermocouple wires 41 and 45 can have improved temperature sensing of the tip electrode and hence the tissue in contact with the tip electrode. For omnidirectional temperature sensing with respect to the intended tissue-contacting surface of the distal end of the tip electrode, distal end of the hole 80a is positioned generally on the longitudinal axis at a distance R (see FIG. 3B) that is equal to about the radius R of the semi-spherical distal end portion of the tip electrode. In the illustrated embodiment, the blind hole 80a has a proximal section 81 and an angled distal section 83 that is separately drilled with a smaller drill bit. This angled configuration reduces the stress on the thermocouple wires 41 and 45 during their transition from the off axis lumen 30 in the tubing 19 of the intermediate section 14 to a more centered position at the distal end of the blind hole 80a. To that end, a notch 79 is formed in the distal end of the connective tube 60a so as to avoid the wires 41 and 45 rubbing against a distal edge of the connective tubing. The wires 41 and 45 of the wire pair are electrically isolated from each other except at their distal ends where they contact and are twisted together, covered with a short piece of plastic tubing 63, e.g., polyimide, and covered with epoxy. The plastic tubing 63 is then attached in the hole 104 of the plug 44, by epoxy or the like.

The irrigation fluid is transferred to the intermediate section 14 by an infusion tube segment 88 (FIG. 2A) that extends through the central lumen 18 of the catheter body 12 and terminates in the proximal portion of the lumen 35 of the intermediate section 14. The proximal end of the infusion tube segment 88 extends through the control handle 16 and terminates in a luer hub 90 (FIG. 1) or the like at a location proximal to the control handle. In practice, fluid may be injected by a pump (not shown) into the infusion tube segment 88 through the luer hub 90, and flows through the segment 88, through the lumen 35, into the fluid cavity 54 in the tip section 36 and exits the distal end of the flow directing member 21 to cool the tip electrode by convention heat loss as described herein. The infusion tube segments may be made of any suitable material, and is preferably made of polyimide tubing. A suitable infusion tube segment has an outer diameter of from about 0.32 inch to about 0.036 inch and an inner diameter of from about 0.14 inch to about 0.032 inch.

Figure 8:
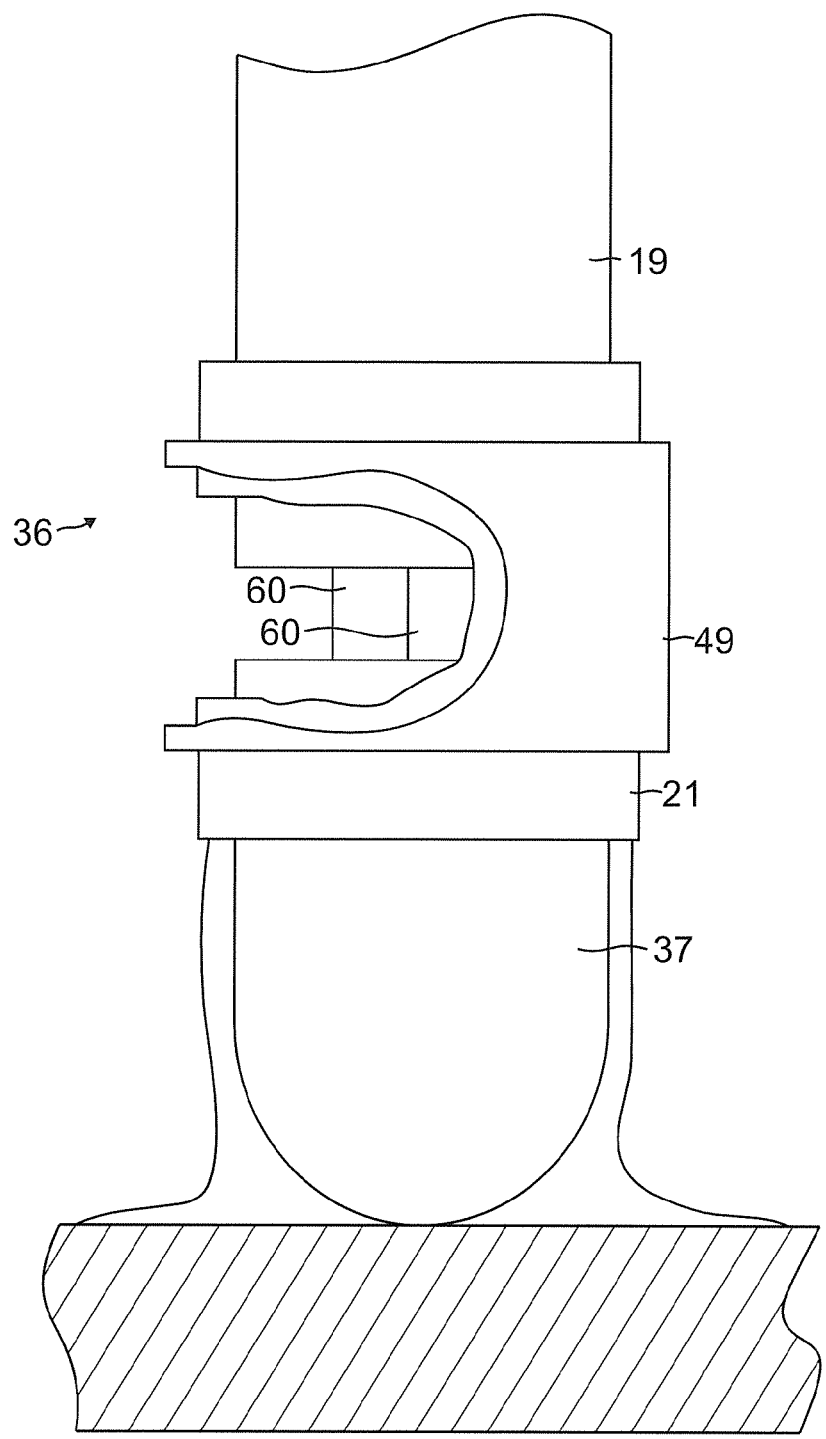
FIG. 8 is a side elevational view of an embodiment of a tip section in contact with tissue during ablation and irrigation, with parts of the flow directing member and ring electrode broken away.

In accordance with a feature of the present invention, the pump maintains the fluid at a positive pressure differential relative to outside of the tip section so as to provide a constant unimpeded flow or seepage of fluid outwardly from the distal end of the flow directing member 21 which continuously flushes the distal end of the tip electrode (see FIG. 8).

Figure 5:
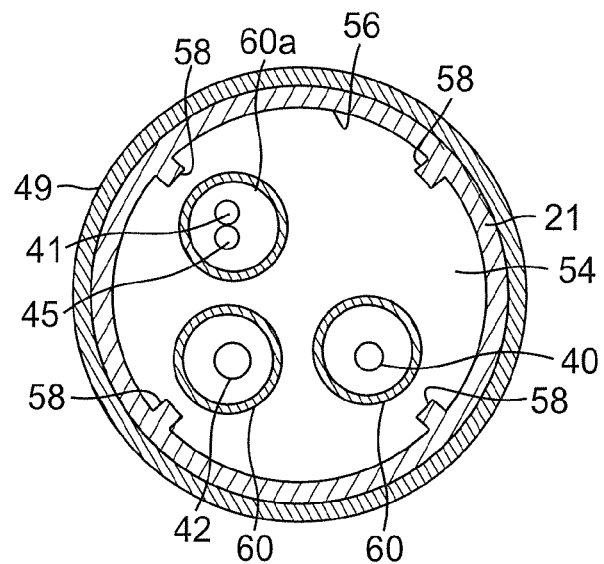
FIG. 5 is a longitudinal cross-sectional view of an embodiment of the tip section of FIGS. 3A and 3B, taken along line 5-5.
Figure 6:
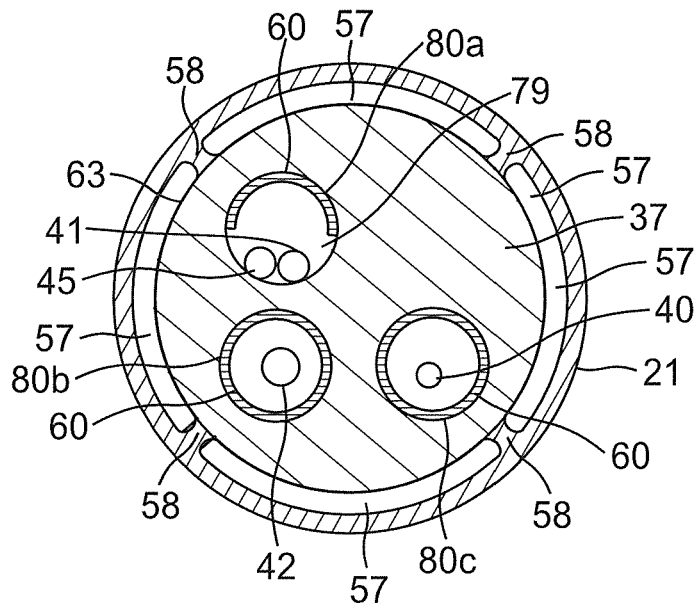
FIG. 6 is a longitudinal cross-sectional view of an embodiment of the tip section of FIGS. 3A and 3B, taken along line 6-6.
Figure 13:
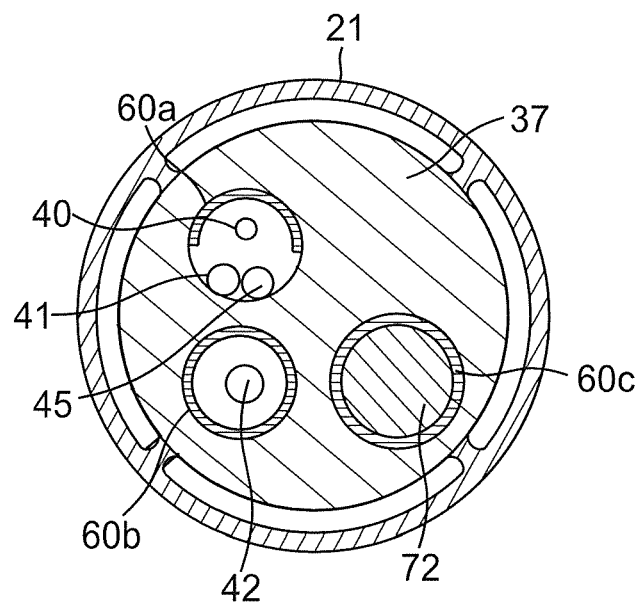
FIG. 13 is a longitudinal cross-sectional view of an embodiment of the tip section of FIG. 10, taken along line 13-13.
Figure 6A:
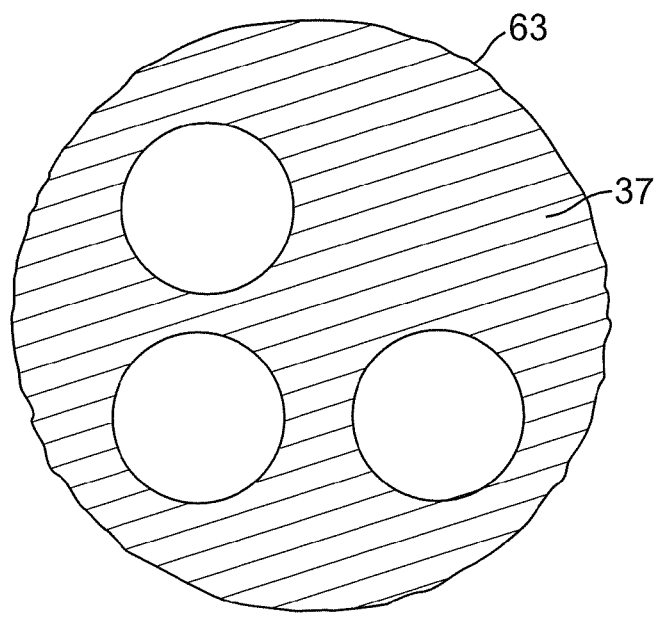
FIG. 6A is a longitudinal cross-sectional view of another embodiment of a tip electrode.
Figure 6B:
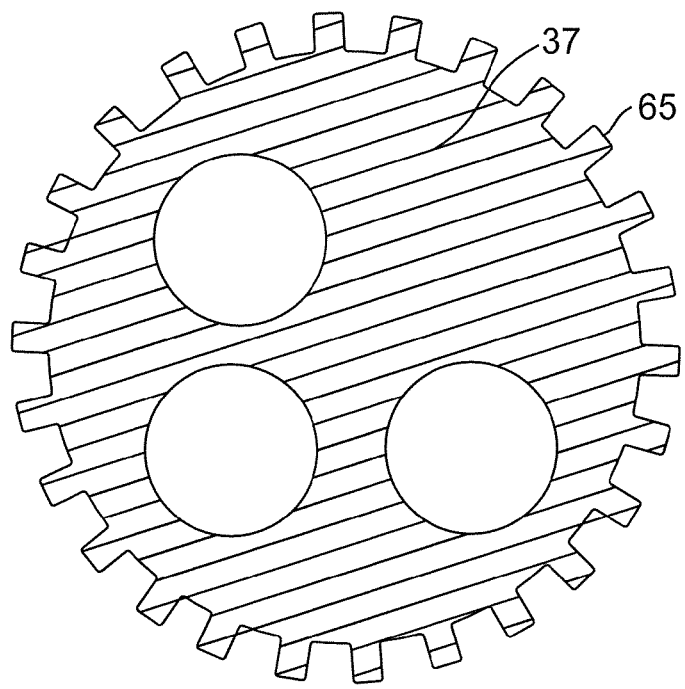
FIG. 6B is a longitudinal cross-sectional view of yet another embodiment of a tip electrode.
Figure 7:
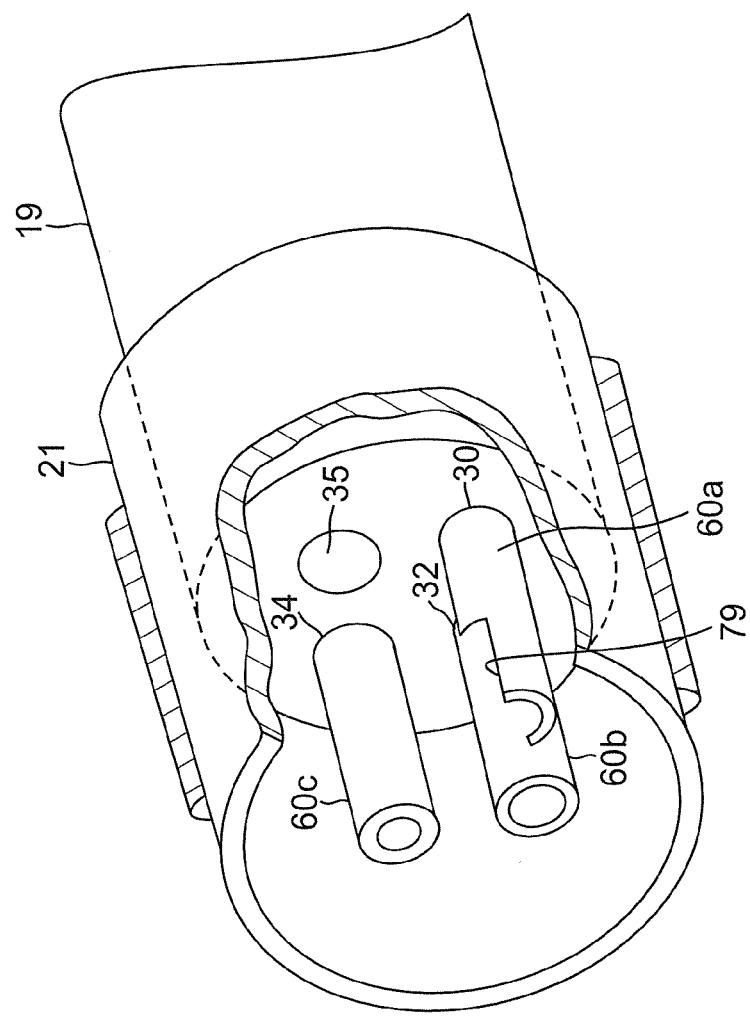
FIG. 7 is a perspective view of an embodiment of a flow directing member mounted on a distal end of an intermediate section, with connective tubes.
Figure 10:
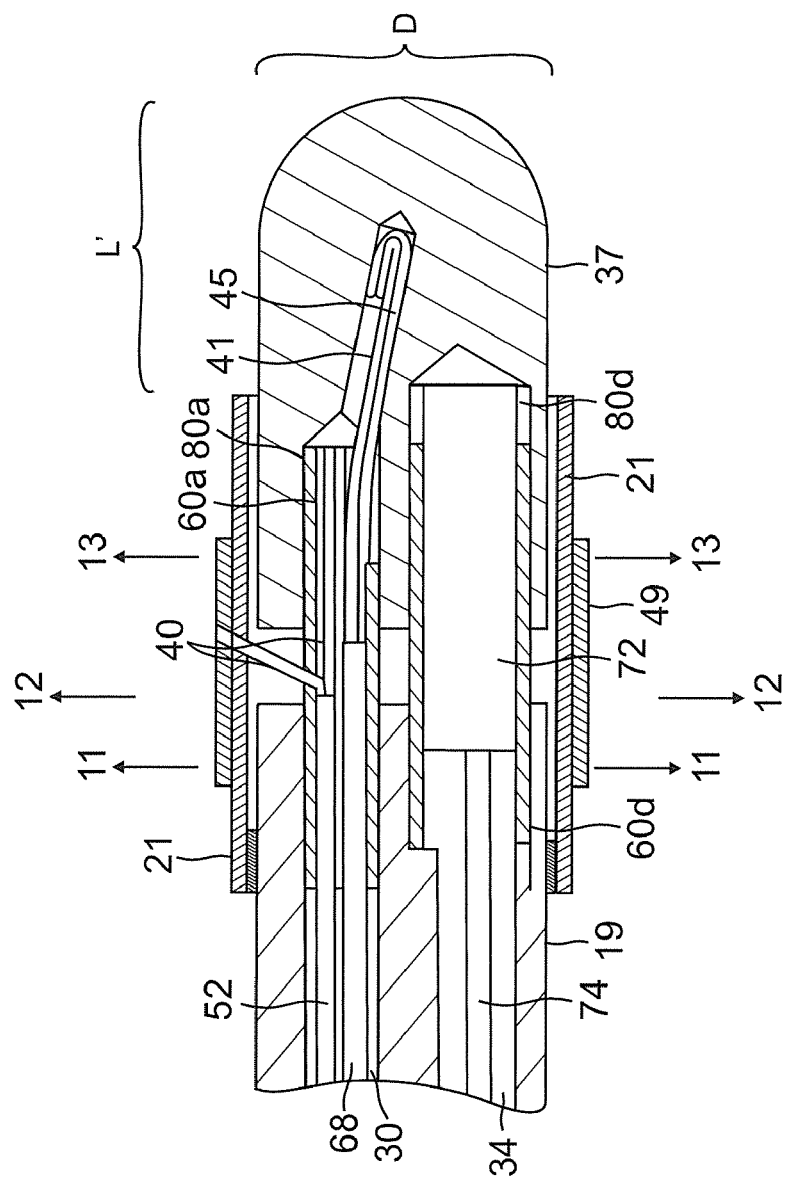
FIG. 10 is a side cross-sectional view of another embodiment of a catheter according to the invention, including a junction between the intermediate section and a tip section, taking along the first diameter.

In an alternative embodiment, the tip section 36 carries an electromagnetic location sensor 72 situated in a blind hole 80d, as illustrated in FIG. 10. The electromagnetic location sensor 72 is connected to an electromagnetic location sensor cable 74. As shown in FIGS. 2A and 5, the sensor cable 74 extends through the lumen 35 of the tip section 36, through the central lumen 18 of the catheter body 12, and into the control handle 16. The sensor cable 74 then extends out the proximal end of the control handle 16 within an umbilical cord 78 (FIG. 1) to a sensor control module 75 that houses a circuit board (not shown). Alternatively, the circuit board can be housed within the control handle 16, for example, as described in U.S. patent application Ser. No. 08/924,616, entitled "Steerable Direct Myocardial Revascularization Catheter", the disclosure of which is incorporated herein by reference. The sensor cable 74 comprises multiple wires encased within a plastic covered sheath. In the sensor control module 75, the wires of the sensor cable 74 are connected to the circuit board. The circuit board amplifies the signal received from the sensor 72 and transmits it to a computer in a form understandable by the computer by means of the sensor connector 77 at the proximal end of the sensor control module 75, as shown in FIG. 1. Because the catheter can be designed for single use only, the circuit board may contain an EPROM chip which shuts down the circuit board approximately 24 hours after the catheter has been used. This prevents the catheter, or at least the electromagnetic location sensor, from being used twice. An electromagnetic mapping sensor 72 may have a length of from about 6 mm to about 7 mm and a diameter of about 1.3 mm.

Figure 9A:
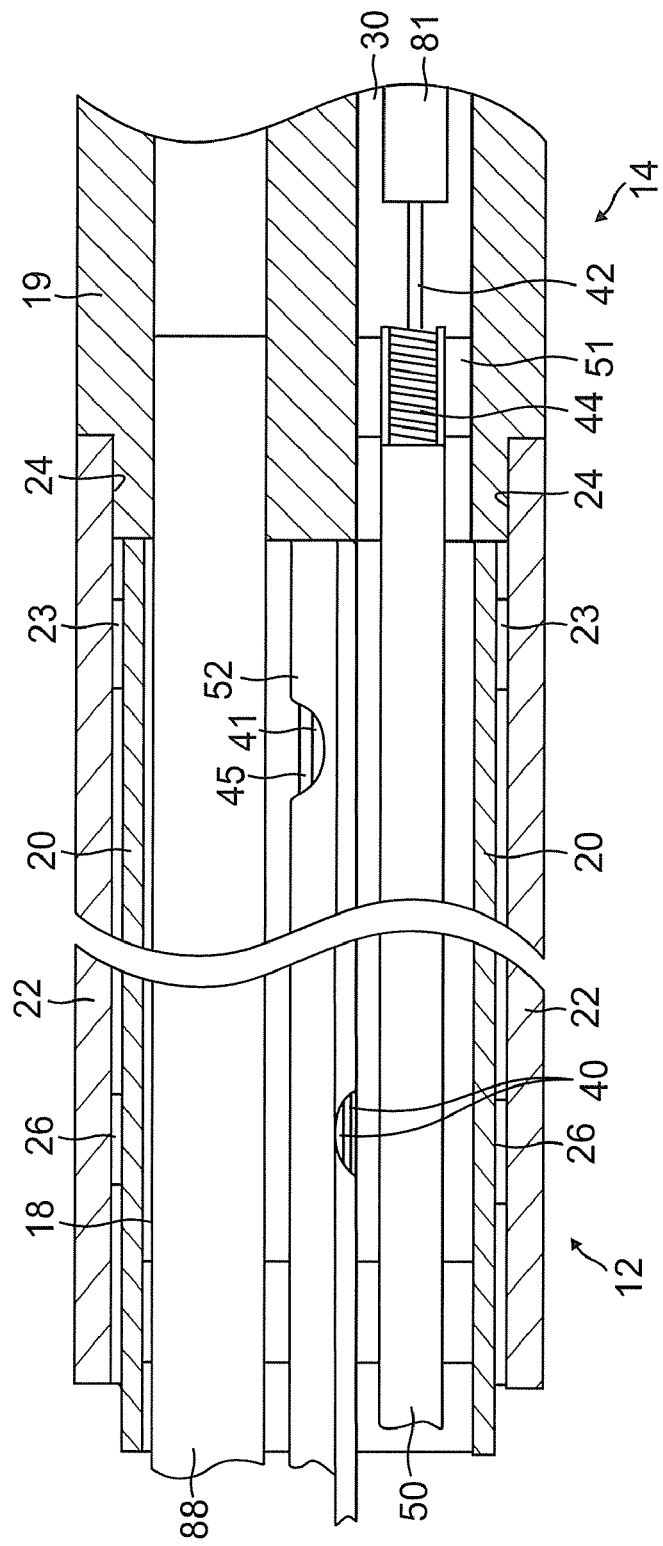
FIG. 9A is a side cross-sectional view of another embodiment of a catheter according to the invention, including a junction between a catheter body and an intermediate section, taken along a first diameter.
Figure 9B:
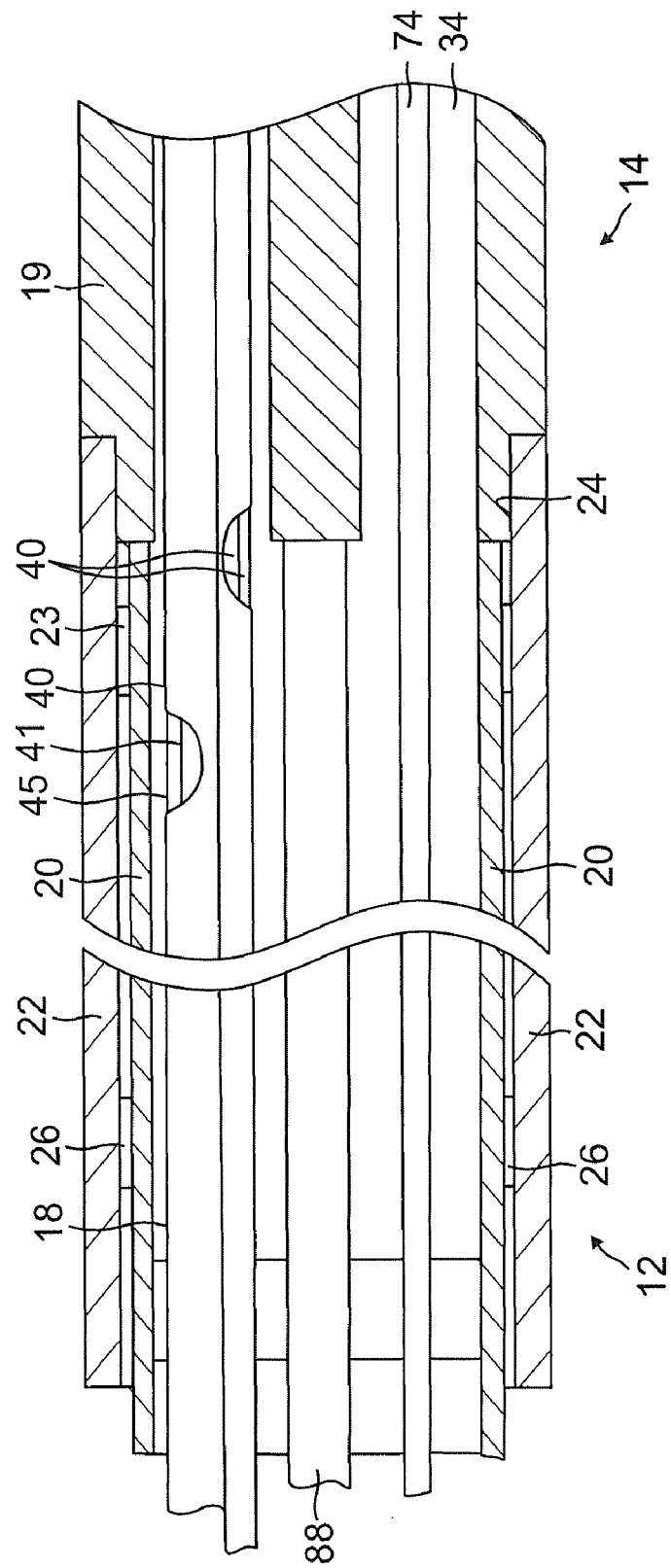
FIG. 9B is a side cross-sectional view of an embodiment of a catheter according to the invention, including the junction between the catheter body and the intermediate section, taken along a second diameter generally perpendicular to the first diameter of FIG. 9A.
Figure 11:
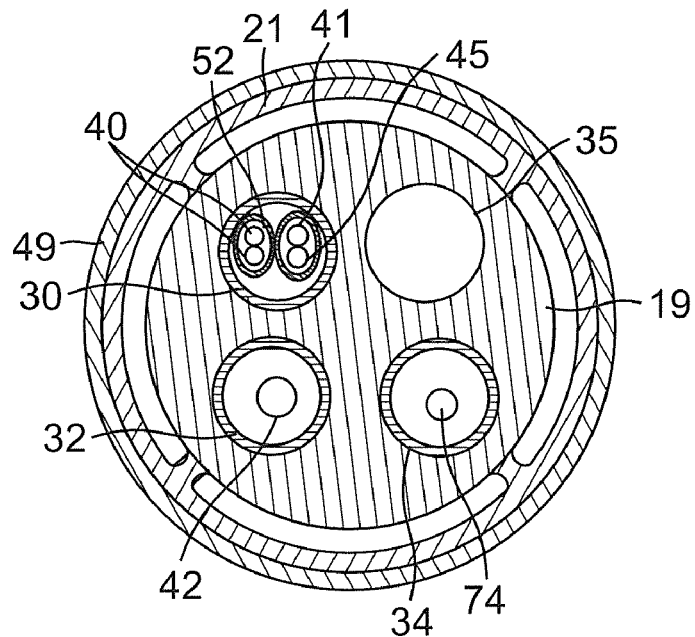
FIG. 11 is a longitudinal cross-sectional view of an embodiment of the tip section of FIG. 10, taken along line 11-11.
Figure 12:
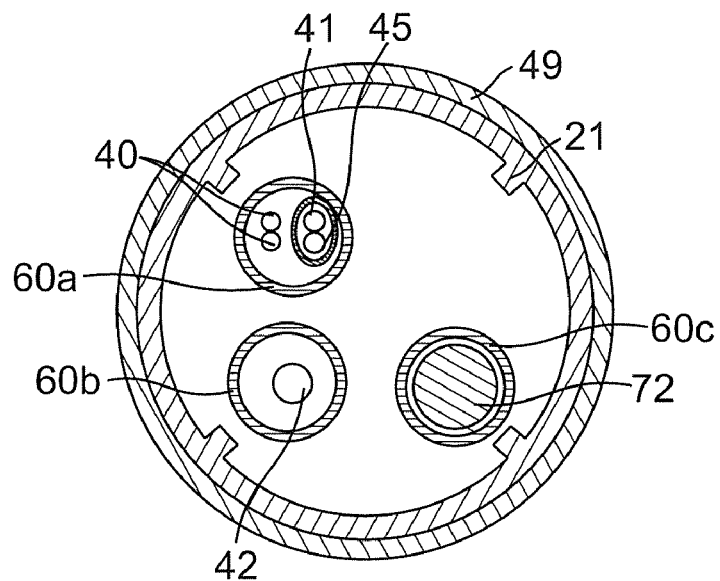
FIG. 12 is a longitudinal cross-sectional view of an embodiment of the tip section of FIG. 10, taken along line 12-12.

In this embodiment, the lead wires 40 extend through the lumen 30 along with the thermocouple wires 41 and 45, so that the sensor cable 74 can occupy the lumen 34 (see FIGS. 9B and 11). As illustrated in FIG. 10, the lumen 34 is trepanned at its distal end to accommodate the electromagnetic location sensor 74, a proximal portion of which extends into the lumen 34 and a distal portion of which extends into an enlarged blind hole 80d lined by a larger connective tube 60d.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. The instant catheter may be manufactured using materials suitable for use on blood contacting medical devices. Tip electrode size and shape may vary depending on intended catheter size and as required for sufficient cooling, component placement, and ablation effectiveness. The thin walled tube used for flow control may be of any material that is stiff enough to provide the required channeling of fluids while maintaining minimal wall thickness. The catheter may be nondeflectable, or deflectable by means of puller wire(s), magnetic steering or a deflectable guiding sheath.

Accordingly, the foregoing description should not be read as pertaining only to the precise structures described and illustrated in the accompanying drawings, but rather should be read consistent with and as support to the following claims which are to have their fullest and fair scope.

What is claimed is:

1. An irrigated tip catheter comprising:
   a catheter body;
   a control handle proximal to the catheter body;
   a deflectable section distal of the catheter body;
   a tip electrode distal of the deflectable section, the tip electrode having an outer surface;
   a generally tubular member positioned at least partially over the tip electrode to direct fluid to flow over at least a portion of the outer surface, wherein the tubular member is mounted over at least a portion of a proximal end of the tip electrode and a distal end of the deflectable section, the tubular member having an inner surface spaced apart from the outer surface of the tip electrode to provide at least one fluid channel for the fluid to flow over the outer surface of the tip electrode;
   a cavity defined by the proximal end of the tip electrode, the distal end of the deflectable section, and the inner surface of the tubular member, wherein fluid entering the cavity is directed to the outer surface of the tip electrode; and
   at least one connective tube extending through the cavity to isolate components extending between the tip electrode and the deflectable section from exposure to the fluid.

2. An irrigated tip catheter of claim 1, wherein the tubular member is supported away from the outer surface of the tip electrode by at least one rib to provide at least one fluid channel between the inner surface of the tubular member and the outer surface of the tip electrode.

3. An irrigated catheter of claim 1, wherein one of the at least one connective tube is notched at its distal end to protect the components extending therethrough.

4. An irrigated catheter of claim 1, wherein the outer surface of the tip electrode is texturized.

5. An irrigated catheter of claim 1, wherein fins are provided on the outer surface of the tip electrode.

6. An irrigated catheter of claim 1, wherein the tubular member covers at least a proximal edge of the tip electrode.

7. An irrigated catheter of claim 1, further comprising a temperature sensing means positioned at or near a center of the tip electrode.

8. An irrigated catheter of claim 7, wherein the temperature sensing means comprises wires whose distal ends are positioned at or near a center of a semi-spherically configured distal end of the tip electrode for omnidirectional temperature sensing.

9. An irrigated catheter of claim 1, further comprising a temperature sensing means positioned to sense temperature omnidirectionally with respect to a tissue-contacting surface of the tip electrode.

10. An irrigated catheter of claim 1, wherein the tubular member is constructed of polyetheretherketone.

11. An irrigated tip catheter comprising:
    a catheter body;
    a tip electrode distal of the catheter, the tip electrode having an outer surface;
    a flow directing member comprising a generally tubular member having an inner surface spaced apart from the outer surface of the tip electrode and a distal portion in a generally surrounding relationship with at least a proximal end of the tip electrode, the flow directing member providing at least one fluid channel to direct fluid transferred by the catheter body to flow over the outer surface of the tip electrode;
    a cavity defined by the proximal end of the tip electrode, a distal end of the catheter body, and the inner surface of the tubular member, wherein fluid entering the cavity is directed to contact the outer surface of the tip electrode; and
    at least one connective tube extending through the tubular member and cavity to isolate components extending into the tip electrode from exposure to the fluid.

12. An irrigated tip catheter of claim 11, wherein the flow directing member is configured to direct the fluid to contact at least a proximal face and a circumferential surface of the tip electrode.

13. An irrigated tip catheter of claim 11, wherein the flow directing member is configured to direct the fluid to flow in an axial direction along the outer surface of the tip electrode.

14. An irrigated tip catheter of claim 11, wherein the outer surface of the tip electrode is texturized to increase contact between the fluid and the tip electrode.

15. An irrigated tip catheter of claim 11, further comprising a deflectable section between the catheter body and the tip electrode.

16. An irrigated tip catheter of claim 11, further comprising an electromagnetic location sensor.

* * * * *